(12) United States Patent
Norman et al.

(10) Patent No.: US 7,622,268 B2
(45) Date of Patent: Nov. 24, 2009

(54) METHODS AND ASSAYS FOR DETECTING GP73-SPECIFIC AUTOANTIBODIES

(75) Inventors: Gary L. Norman, San Clemente, CA (US); Zakera Shums, San Diego, CA (US)

(73) Assignee: INOVA Diagnostics, Inc., San Diego, CA (US)

( * ) Notice: Subject to any disclaimer, the term of this patent is extended or adjusted under 35 U.S.C. 154(b) by 0 days.

(21) Appl. No.: 11/977,826

(22) Filed: Oct. 26, 2007

(65) Prior Publication Data

US 2008/0166738 A1    Jul. 10, 2008

Related U.S. Application Data

(60) Provisional application No. 60/855,015, filed on Oct. 27, 2006.

(51) Int. Cl.
    *G01N 33/53* (2006.01)
(52) U.S. Cl. .................. 435/7.1; 435/7.92; 436/501; 436/518
(58) Field of Classification Search ............. 435/7.1, 435/7.92–7.95, 973; 436/164, 172, 501, 436/518, 811
    See application file for complete search history.

(56) References Cited

U.S. PATENT DOCUMENTS

| | | | |
|---|---|---|---|
| 4,981,785 A | 1/1991 | Nayak | |
| 5,358,691 A | 10/1994 | Clark et al. | |
| 5,885,530 A | 3/1999 | Babson et al. | |
| 6,159,750 A | 12/2000 | Edmonds | |
| 6,548,302 B1 * | 4/2003 | Mao et al. | 435/455 |
| 6,645,725 B2 | 11/2003 | Yeaman | |
| 2005/0037022 A1 * | 2/2005 | Rosen et al. | 424/192.1 |
| 2005/0112711 A1 | 5/2005 | Romano et al. | |

OTHER PUBLICATIONS

Bachert et al., "Endosomal Trafficking and Proprotein Convertase Cleavage of *cis* Golgi Protein GP73 Produces Marker for Hepatocellular Carcinoma", *Traffic* 8(10):1415-1423 (Jul. 2007).
Block et al., "Use of Targeted Glycoproteomics to Identify Serum Glycoproteins That Correlate with Liver Cancer in Woodchucks and Humans", *PNAS* 102(3):779-784 (Jan. 18, 2005).
Block et al., "Surrogate Markers of Efficacy For Medical Treatment of Viral Hepatitis", *Biotechnology Healthcare* pp. 42-48 (Oct. 2004).
Chignard et al., "Proteomics for Hepatocellular Carcinoma Marker Discovery", *Gastroenterology* 127(5):S120-S125 (Nov. 2004).
Gish, "Hepatocellular Carcinoma: Overcoming Challenges in Disease Management", *Clinical Gastroenterology and Hepatology* 4(3):252-261 (Mar. 2006).
Kladney et al, "Expression of GP73, A Resident Golgi Membrane Protein, in Viral and Nonviral Liver Disease", *Hepatology* 35(6):1431-1440 (Jun. 2002).
Iftikhar et al., "Disease- and Cell-Specific Expression of GP73 in Human Liver Disease", *American Journal of Gastroenterology* 99(6):1087-1095 (Jun. 2004).
Maitra et al., "GP73 and Liver Disease: A (Golgi) Complex Enigma", *American Journal of Gastroenterology* 99(6):1096-1098 (Jun. 2004).
Marrero et al., "Newer Markers for Hepatocellular Carcinoma", *Gastroenterology* 127(5):S113-S119 (Nov. 2004).
Paradis et al., "Identification of a New Marker of Hepatocellular Carcinoma by Serum Protein Profiling of Patients with Chronic Liver Disease", *Hepatology* 41(1):40-47 (Jan. 2005).
Puri et al., "Cycling of Early Golgi Proteins Via the Cell Surface and Endosomes Upon Lumenal pH Disruption", *Traffic* 3(9):641-653 (2002).
Schwegler et al., "SELDI-TOF MS Profiling of Serum for Detection of the Progression of Chronic Hepatitis C to Hepatocellular Carcinoma", Hepatology 41(3):634-642 (Mar. 2005).
Xiao et al., "Cartilage Oligomeric Matrix Protein Expression in Hepatocellular Carcinoma and the Cirrhotic Liver", *Journal of Gastroenterology and Hepatology* 19:296-302 (2004).
Lutz et al., Humoral Immune Reactivity to Feline Leukemia Virus and Associated Antigens in Cats Naturally Infected with Feline Leukemia Virus, Cancer Research 40, 3642-3651. (Oct. 1980).
Marrero et al., GP73, a resident Golgi glycoprotein, is a novel serum marker for hepatocellular carcinoma, Journal of Hepatolgoy 43, 1007-1012 (2005).
Wright et al., A concise review of serum markers for hepatocellular cancer. Cancer Detection and Prevention 31, 35-44. (2007). See pp. 37-38.
Kladney et al. "Upregulation of Golgi protein GP73 by adenovirus infection requires the EIA CtBP interaction domain" *Virology* 301:236-46, 2002.
Kladney et al. GP73 a novel Golgi localized protein upregulated by viral infection: *Gene* 249:53-65, 2000.

* cited by examiner

*Primary Examiner*—Gailene R Gabel
*Assistant Examiner*—Gary W Counts
(74) *Attorney, Agent, or Firm*—Laurie A. Axford; The Nath Law Group (57) ABSTRACT

The present invention provides a method for detecting autoantibodies in a subject which reacts with a GP73 antigen. Increased levels of GP73-specific autoantibodies in a sample from the subject which bind to GP73 antigen are indicative of liver disease in the subject.

1 Claim, 4 Drawing Sheets

Total number of Patients = 187
Non cirrhotics = 91
Cirrhotics = 96

Non cirrhotics = 92

|  | TOTAL POS | < 11.9 COMP | 12 - 14.9 COMP | >15 COMP |
|---|---|---|---|---|
| COMP | 24 (26%) | 0 | 14 | 10 |
| GP73 autoantigen | 5 (5%) | 4 | 1 | 0 |
| Anti-GP73 Autoantibody | 60 (66%) | 44 | 10 | 6 |

Taking the COMP c/o to be 12 units>
Pos on all 3 tests = 1/ 92 ( 1 % )
Pos on any 2 tests = 19/92 ( 21%)
Pos on any 1 test = 48/92 ( 53%)
Neg on all 3 tests = 24/92 (26%)

Taking the COMP c/o to be 15 units=>
Pos on all 3 tests = 0/ 92 ( 0 % )
Pos on any 2 tests = 11/92 ( 12%)
Pos on any 1 test = 53/92 ( 58%)
Neg on all 3 tests = 28/92 (30%)

Cirrhotics = 95

|  | TOTAL POS | < 11.9 COMP | 12 - 14.9 COMP | >15 COMP |
|---|---|---|---|---|
| COMP | 60 (63%) | 0 | 18 | 42 |
| GP73 autoantigen | 29 (30%) | 10 | 4 | 15 |
| Anti-GP73 Autoantibody | 81 (84%) | 29 | 15 | 37 |

Taking the COMP c/o to be 12 units>
Pos on all 3 tests = 17/ 95 ( 17 % )
Pos on any 2 tests = 49/95 ( 51%)
Pos on any 1 test = 27/95 ( 28%)
Neg on all 3 tests = 2/95 (2%)

Taking the COMP c/o to be 15 units=>
Pos on all 3 tests = 12/ 95( 13 % )
Pos on any 2 tests = 35/95 ( 36%)
Pos on any 1 test = 44/95 ( 45%)
Neg on all 3 tests = 4/95 (4%)

Normals - gp 73
Promedx Total = 80
Auto ag GP73 Highest O.D. = 0.649. Therefore c/o = 0.65
Auto ab GP73 Highest O.D. = 1.237 Therefore c/o = 1.3
Specificty based on 80 samples assumed to be 100% for both auto ag and auto ab test.

Normals-COMP
Promedx Total = 80 ( same specimens from gp73 test)
14/80 (17.5%) specimens had > 15 units for COMP

| COMP c/o= > 15.0 units | Non cirrhotics | Cirrhotics |
|---|---|---|
| 1 test | 58 | 45 |
| 2 tests | 12 | 36 |
| 3 tests | 0 | 13 |

METHODS AND ASSAYS FOR DETECTING GP73-SPECIFIC AUTOANTIBODIES

CROSS REFERENCE TO RELATED APPLICATION

This application is based on, and claims the benefit of, U.S. Provisional Application No. 60/855,015, filed Oct. 27, 2006.

TECHNICAL FIELD

The present invention is in the field of autoimmunity and relates to the detection and quantitation of GP73-specific antoantibodies for diagnosing and monitoring liver disease in a subject.

BACKGROUND OF THE INVENTION

Hepatocellular carcinoma (HCC) is the primary malignancy of the liver, which appears to be rising in incidence in the United States and other developed western countries. The prevalence of HCC worldwide parallels that of viral hepatitis, and the majority of cases are associated with hepatitis B (HBV) and hepatitis C (HCV). It has been observed that patients with longstanding chronic hepatitis or cirrhosis who have hepatitis B, C, or hereditary hemochromatosis have the highest risk of developing HCC. Patients with longstanding alcoholic cirrhosis are also at risk for developing this type of malignancy.

Diagnosis of hepatocellular carcinoma is, however, extremely challenging as most of the patients who are developing HCC have no symptoms other than those related to their longstanding liver disease. Once symptoms such as abdominal pain, weight loss, early satiety, jaundice and a palpable mass in the upper abdomen, have developed, HCC has most likely advanced to a stage that is too late for an effective treatment. As a result, the current median survival following diagnosis is only about 6 to 20 months.

The current clinical methods are in some ways ineffective for early diagnosis of HCC. Most HCCs are first suspected based on the imaging results of computerized axial tomography (CAT) scans or ultrasound scans. However, liver imaging has a high false positive rate due to low sensitivity and specificity. Accordingly, the diagnosis often has to be confirmed by performing an invasive needle biopsy.

Another commonly used diagnostic method is based on the blood level of alpha-fetoprotein (AFP), a normal serum protein synthesized by fetal liver cells. It is often measured as a part of screening in patients with chronic hepatitis B or chronic hepatitis C and cirrhosis. Since there is a good correlation between elevated levels of AFP and the occurrence of HCC, determination of AFP levels is often included as a serum marker of the disease. However, AFP as a sole indicator of HCC is often of very limited value for diagnosing HCC, since elevated AFP levels are not specific for HCC. Further complications come from that fact that not all HCC patients exhibit an elevated level of AFP. In fact, it has been shown that only about 70% of patients with HCC have elevated AFP levels.

As such, there is a need for an improved diagnostic assay for early detection of HCC. Accordingly, the present invention relates to an assay that exhibits a strong correlation between the level of GP73-specific autoantibodies and HCC, which can be used as a biological marker for monitoring and diagnosis of HCC.

SUMMARY OF THE INVENTION

The present invention provides a method for detecting GP73-specific autoantibodies. In one embodiment, the method comprises the steps of: preparing a GP73 antigen comprising a polypeptide having an epitope from a GP73 protein; reacting the GP73 antigen with a sample from the subject; and detecting GP73-specific autoantibodies in the sample that bind to the GP73 antigen. The method can be applied to aid in the diagnosis of a subject suspected of having a liver disease, especially HCC. The method can also be used to monitor the status of a subject having HCC for better treatment.

In an alternative embodiment, the method for diagnosing liver disease in a subject comprises the steps of (a) obtaining a sample from the subject suspected of liver disease, (b) incubating a GP73 antigen with the sample, and (c) detecting autoantibody reactivity with the GP73 antigen in the sample. Autoantibody reactivity may be determined by immunoassays such as immunometric or competitive assays.

The present invention also provides an assay for detecting GP73-specific autoantibodies in a sample from a subject suspected of containing the autoantibodies. In one embodiment, the assay is an immunometric assay, which comprises the steps of: (a) immobilizing a GP73 antigen on a solid support; (b) contacting a sample suspected of containing GP73-specific autoantibodies to the GP73 antigen bound on the solid support; (c) adding a labeled antibody to the solid support, wherein the labeled antibody recognizes the GP73-specific autoantibody and is part of a signal producing system; (d) separating free labeled antibody from bound antibody, and (e) measuring the signal generated by the solution containing the solid support. When the subject is a human, the labeled antibody is an anti-human immunoglobulin.

In another embodiment, the assay is a competitive immunoassay, comprising the steps of: (a) preparing a reaction mixture by incubating a labeled antibody which is bound to a GP73 antigen with a sample from a subject suspected of containing a GP73-specific autoantibody, wherein the labeled antibody is part of a signal producing system; (b) separating bound labeled antibodies from free antibodies; and (c) measuring the signal generated by the labeled antibody.

In still another embodiment, the assay is a competitive immunoassay, which comprises the steps of: (a) preparing a reaction mixture by incubating a first antibody which is bound to a GP73 antigen with a sample from a subject suspected of containing a GP73-specific autoantibody; (b) adding a second antibody to the reaction mixture, wherein the second antibody recognizes the first antibody, and wherein the second antibody is labeled and part of a signal producing system; (c) separating free labeled second antibody from bound antibody; and (d) measuring the signal generated by the second antibody in the reaction mixture.

In some embodiments where the antibody is enzyme labeled, the additional steps of adding a substrate to the GP73-antigen and GP73-specific autoantibody complexes to react with the enzyme-labeled antibody, followed by incubation, are performed prior to measuring the generated signal.

The present invention further provides a diagnostic kit for detecting GP73-specific autoantibodies in a sample from a subject suspected of containing the autoantibodies. In one embodiment, the diagnostic kit comprises one or more reagents for detecting GP73-specific autoantibodies in a sample. The reagents include some of those described herein above, for example, a GP73 antigen and a labeled antibody such as a labeled anti-human immunoglobulin. In another embodiment, the diagnostic kit further comprises a positive control that indicates the level of GP73-specific autoantibodies in a subject. In still another embodiment, the diagnostic kit further comprises instructions for using the kit for detecting the level of GP73-specific autoantibodies. The instructions are for diagnosing and/or monitoring liver disease in the subject based at least partially on the level of GP73-specific autoantibodies. The instructions may also be instructions required by the U.S. Food and Drug Administration for an in vitro diagnostic kit.

The present invention also provides a panel assay for the diagnosis of liver disease, comprising two or more assays for detecting two or more biological markers. In one embodiment, the panel assay is to detect two biological markers. The first biological marker is GP73-specific autoantibodies whereas the second biological marker is a GP73 antigen, COMP, or AFP. In another embodiment, the panel assay is to detect three biological markers. The first biological marker is GP73-specific autoantibodies whereas the second and third biological markers are independently selected from the group consisting of GP73 antigen, COMP, and AFP.

Other aspects of the invention are described throughout the specification.

BRIEF DESCRIPTION OF THE DRAWINGS

FIGS. 4 A-B shows the distribution of patients according to their positive responses to the three diagnostic tests.

DETAILED DESCRIPTION OF THE INVENTION

The present invention relates in part, to a method for detecting GP73-specific autoantibodies. In one embodiment, the method comprises the steps of: preparing a GP73 antigen such as a polypeptide having an epitope from the GP73 protein; reacting the GP73 antigen with a sample from the subject; and detecting GP73-specific autoantibodies in the sample that bind to the GP73 antigen. The method can be applied to aid in the diagnosis of a subject suspected of having liver disease, especially HCC. The method can also be applied in monitoring the status of a subject having HCC during treatment.

In the description that follows, a number of terms used in the field of molecular biology, immunology and medicine are extensively utilized. In order to provide a clearer and consistent understanding of the specification and claims, including the scope to be given such terms, the following non-limiting definitions are provided.

When the terms "one," "a," or "an" are used in this disclosure, they mean "at least one" or "one or more," unless otherwise indicated.

The term "antibody" refers to a molecule which is capable of binding an epitope or antigenic determinant. The term "antibody" includes whole antibodies and antigen-binding fragments thereof, including single-chain antibodies. Such antibodies include human antigen binding antibody and antibody fragments, including, but not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. The antibodies may be from any animal origin including birds and mammals, e.g., human, murine, rabbit, goat, guinea pig, camel, horse and the like.

The term "antigen" refers to a molecule capable of being bound by an antibody or a T cell receptor (TCR) if presented by MHC molecules. An antigen may be additionally capable of being recognized by the immune system and/or being capable of inducing a humoral immune response and/or cellular immune response leading to the activation of B- and/or T-lymphocytes. An antigen may have one or more epitopes (B- and T-epitopes). Antigens as used herein may also be mixtures of several individual antigens.

The term "antigenic determinant" refers to a portion of an antigen that is specifically recognized by either B- or T-lymphocytes. Antigenic determinants or epitopes are those parts of an antigen that are recognized by antibodies, or in the context of an MHC, by T-cell receptors. An antigenic determinant contains one or more epitopes.

The term "autoantibody" refers to an antibody directed against self-protein, carbohydrate or nucleic acid.

The term "epitope" refers to a portion of an antigen that is recognized by the immune system, such as an antibody (e.g., an autoantibody), B-lymphocyte, or T-lymphocyte, and thus the particular domain, region or molecular structure to which the antibody, B-lymphocyte, or T-lymphocyte binds.

The term "wild-type" refers to a gene or gene product isolated from a naturally occurring source. A wild-type gene is that which is most frequently observed in a population and is thus arbitrarily designated as the "normal" or "wild-type" form of the gene or gene product. In contrast, the term "modified" or "mutant" refers to a gene or gene product that displays modifications in sequence and/or functional properties (e.g., hypomethylation) when compared to the wild-type gene or gene product. It is noted that naturally occurring mutants can be isolated and identified by the fact that they have altered characteristics, such as physical and biological properties, when compared to the wild-type gene or gene product. A "wild-type" gene product is also commonly referred to as a "native protein."

The term "portion" when in reference to a protein refers to fragments of that protein. The fragments may range in size from two amino acid residues to the entire amino acid sequence minus one amino acid.

The term "subject" refers to an animal, including, but limited to, an ovine, bovine, ruminant, lagomorph, porcine, equine, canine, feline, rodent or primate, for example a human. Typically, the terms "subject" and "patient" are used interchangeably herein in reference, for example, to a mammalian subject, particularly a human subject.

The term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, cells, plasma, interstitial fluid, urine, cerebrospinal fluid, nucleic acid, DNA, tissue, and purified or filtered forms thereof. Environmental samples include environmental material such as surface matter, soil, water, crystals and industrial samples.

The term "control" or "control sample" refers to one or more samples, such as a serum sample, taken from at least one individual who has tested negative for the determinant (e.g., antigens or antibodies) in question. For example, a control for testing for the presence of GP73-specific autoantibodies might be taken from a subject who does not have HCC or any other liver disorder.

GP73 Antigen

A variety of GP73 proteins, polypeptides, and chemical analogs are suitable for use in the present invention as a GP73 antigen for the detection of GP73-specific autoantibodies. In one aspect, the GP73 antigen is a GP73 protein or fragments thereof from any species, including, but not limited to, an ovine, bovine, ruminant, porcine, equine, canine, feline, rodent or primate, for example a human. The GP73 protein may be purified from natural sources or produced using protein engineering technologies, which may have different post-translation modifications compared to the protein from natural sources. In the present invention, the recombinant GP73 proteins are produced using standard molecular biology protocols that are well known to those skilled in the art.

The native GP73 protein is a 400 amino acid type II Golgi membrane protein with an apparent molecular weight of approximately 73 kDa. The nucleotide and deduced amino acid sequence of the native GP73 is disclosed in Kladney et al., 2000 and in GenBank record Accession No. AF236056. The full-length GP73 cDNA comprises 3042 base pairs and contains a single open reading frame of 1200 base pairs.

The GP73 proteins that are useful in the present invention may also be variants of the wild-type protein. Unless otherwise indicated, the term "GP73" refers both to native GP73 proteins, as well as variants thereof. As used herein, a GP73 variant is a GP73 protein which comprises an amino acid sequence having one or more amino acid substitutions, deletions, and/or additions (such as internal additions and/or GP73 fusion proteins) as compared to the amino acid sequence of a native GP73 protein, but which nonetheless retains GP73 immunological activity. Such functionally or immunologically equivalent variants may occur as natural biological variations (e.g., GP73 polypeptide allelic variants, GP73 polypeptide orthologs, and GP73 polypeptide splice variants), or they may be prepared using known techniques, for example by chemical synthesis or modification, or mutagenesis (e.g., site-directed or random mutagenesis). Thus, for example, an amino acid may be replaced by another which preserves the physicochemical character of the GP73 protein or its epitope(s), e.g. in terms of charge density, hydrophilicity/hydrophobicity, size and configuration and hence preserves the immunological structure. "Addition" variants may include N- or C-terminal fusions as well as intrasequence insertions of single or multiple amino acids. Deletions may be intrasequence or may be truncations from the N- or C-termini.

The variants may have from 1 to 3, to 5, to 10, to 15, to 20, to 25, to 50, to 75, or to 100, or more than 100 amino acid substitutions, insertions, additions and/or deletions, wherein the substitutions may be conservative, or non-conservative, or a combination thereof. Additionally, the GP73 protein of the present invention may comprise at least 10, at least 12, at least 15, at least 20, at least 25, at least 30, at least 35, at least 40, or at least 50 consecutive amino acid residues of a native GP-73 protein. Such a variant is preferably at least about 50%, at least about 60%, at least about 70%, at least about 80%, as lest about 90%, or at least about 95% identical to a native GP73 protein. Furthermore, the GP73 variant may retain immunologically active with an activity of over about 1%, over about 10%, over about 25%, over about 50%, over about 60%, over about 70%, over about 80%, over about 90%, over about 95%, or over about 100% of the immunological activity of the native protein.

Conservative modifications to the amino acid sequence of a GP73 protein generally produce a polypeptide having functional and chemical characteristics similar to those of the original GP73 protein. In contrast, substantial modifications in the functional and/or chemical characteristics of a GP73 protein may be accomplished by selecting substitutions in the amino acid sequence of the GP73 protein that differ significantly in their effects on maintaining (a) the structure (secondary, tertiary, and/or quandary) in the area of the substitution or (b) the charge or hydrophobicity of the molecule at the target site. Amino acid sequence modifications can be accomplished by chemical and biological peptide and protein synthetic methods that are well know in the art.

Desired amino acid substitutions (whether conservative or non-conservative) can be determined by those skilled in the art at the time such substitutions are required. For example, amino acid substitutions can be used to identify important residues, to modulate the biological activity of a GP73 protein, e.g., the binding interactions with a GP73-specific autoantibody, or to decrease unwanted non-specific binding interactions with other molecules in a sample. Suitable amino acid substitutions include, but are not limited to, substituting Ala with Val, Leu, or Ile; substituting Arg with Lys, Gln, or Asn; substituting Asn with Gln; substituting Asp with Glu; substituting Cys with Ser or Ala; substituting Gln with Asn; substituting Glu with Asp; substituting His with Asn, Gln, Lys, or Arg; substituting Ile with Leu, Val, Met, Ala, Phe, or Norleucine; substituting Leu with Norleucine, Ile, Val, Met, Ala, or Phe; substituting Lys with Arg, 1,4-diamino-butyric acid, Gln, or Asn; substituting Met with Leu, Phe, or Ile; substituting Phe with Leu, Val, Ile, Ala, or Tyr; substituting Pro with Ala; substituting Ser with Thr, Ala, or Cys; substituting Thr with Ser; substituting Trp with Tyr or Phe; substituting Tyr with Trp, Phe, Thr, or Ser; and substituting Val with Ile, Met, Leu, Phe, Ala, or Norleucine. The selection of an amino acid for replacement can also be guided by its hydropathic index and/or hydrophilicity.

In addition, the GP73 polypeptide may be fused to a homologous polypeptide to form a homodimer or to a heterologous polypeptide to form a heterodimer. Heterologous polypeptides include, but are not limited to: an epitope to allow for the detection and/or isolation of a GP73 fusion polypeptide, such as, polyhistine at either C- or N-terminal to ease the purification; an enzyme or portion thereof which is catalytically active; a polypeptide which promotes oligomerization, such as a leucine zipper domain; and a polypeptide which increases stability, such as an immunoglobulin constant region.

Fusions can be made either at the amino-terminus or at the carboxyl-terminus of a GP73 polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a protease to allow for the separation of the fused moieties. It will be appreciated that once constructed, the fusion polypeptides can further be derivatized according to the methods described herein.

The GP73 protein of the present invention may also be a GP73 derivative, which is a chemically or biologically modified GP73 protein, including protein post-translation modification, such as acylation (i.e., acetylation or formylation), biotinylation, carboxylation, deamination, glutathionylation, glycosylation, lipidation (i.e., farnesylation, gernylgeranylation, prenylation, myristoylation, palmitoylation, or stearoylation), methylation, phosphorylation, sulphation, fucosylation, and ubiquitination. Unless otherwise indicated, the term "GP73 protein" refers both to native GP73 proteins, and variants and derivatives thereof. A GP73 derivative may be modified in a manner that is different in the type, number, or location of the post-translation modification groups naturally attached to the polypeptide. For example, a GP73 derivative may have the number and/or type of glycosylation altered compared to the native GP73 protein. The resulting GP73 derivative may comprise a greater or a lesser number of N-linked glycosylation sites than the native protein.

The GP73 polypeptide may also be modified by the covalent attachment of one or more polymers. Typically, the polymer selected is water-soluble so that the protein to which it is attached does not precipitate in an aqueous environment, such as a physiological environment. The polymer may be of any molecular weight and may be branched or unbranched. The polymer each typically has an average molecular weight of between about 1 kDa to about 100 kDa.

Suitable water-soluble polymers or mixtures thereof include, but are not limited to, polyalkylene glycol (such as mono-$(C_1-C_{10})$ alkoxy-, aryloxy-polyethylene glycol, poly-(N-vinyl pyrrolidone) polyethylene glycol, propylene glycol homopolymers, or polypropylene oxide/ethylene oxide copolymers), carbohydrate-based polymers (such as dextran or cellulose), polyoxyethylated polyols, and polyvinyl alcohols. Also encompassed by the present invention are bifunctional crosslinking molecules which can be used to prepare covalently attached GP73 polypeptide multimers.

In general, chemical derivatization may be performed under a suitable condition by reacting a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby a GP73 protein becomes attached to one or more polymer molecules, and (b) obtaining the reaction products. The optimal reaction conditions may vary depending upon the GP73 protein selected and chemical reagents used, and are generally determined experimentally. The PEGylation of a polypeptide may be carried out using any of the PEGylation reactions known in the art, including, but not limited to, acylation, alkylation, or Michael addition.

Diagnostic Assay

There are many different types of immunoassays suitable for use in the present invention. Any of the well known immunoassays may be adapted to detect the level of GP73-specific autoantibodies in a sample which react with the GP73 antigen, such as, e.g., enzyme linked immunoabsorbent assay (ELISA), fluorescent immunosorbent assay (FIA), chemical linked immunosorbent assay (CLIA), radioimmuno assay (RIA), immunoblotting, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc. For a review of the different immunoassays which may be used, see: The Immunoassay Handbook, David Wild, ed., Stockton Press, New York, 1994. A competitive immunoassay with solid phase separation or an immunometric assay for antibody testing is particularly suitable for use in the present invention. See, The Immunoassay Handbook, chapter 2.

In one exemplary embodiment of the invention, the diagnostic assay is an immunometric assay for detecting the level of GP73-specific autoantibodies in a sample. In the immunometric assay, a GP73 antigen is immobilized on a solid support directly or indirectly through a capture agent, such as anti-GP73 antibodies. An aliquot of a sample, such as a serum sample, from a subject is added to the solid support and allowed to incubate with the GP73 antigen on the solid phase. A secondary antibody that recognizes a constant region in the autoantibodies present in the sample which have reacted with the GP73 antigen is added. When the subject is a human, this secondary antibody is an anti-human immunoglobulin. The secondary antibody which is specific for IgA, IgG, or IgM heavy chain constant regions may be employed. After separating the solid support from the liquid phase, the support phase is examined for a detectable signal. The presence of the signal on the solid support indicates that autoantibodies to the native GP73 protein present in the sample have bound to the GP73 antigen on the solid support. Increased optical density or radiolabeled signal when compared to the control samples from normal subjects correlates with a diagnosis of HCC in a subject.

Solid supports are known to those skilled in the art and include the walls of wells of a reaction tray (e.g., microtiter plates), test tubes, polystyrene beads, magnetic beads, nitrocellulose strips, membranes, microparticles such as latex particles, glass or silicon chips, sheep (or other animal) red blood cells, duracytes and others. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional molecule which has the ability to attract and immobilize the capture reagent. The additional molecule can include a charged substance that is oppositely charged with respect to the capture reagent itself or to a charged substance conjugated to the capture reagent. As yet another alternative, the molecule can be any specific binding member which is immobilized upon (attached to) the solid support and which has the ability to immobilize the GP73 antigen through a specific binding reaction. The molecule enables the indirect binding of the GP73 antigen to a solid support material before the performance of the assay or during the performance of the assay.

The signal producing system is made up of one or more components, at least one of which is a label, which generate a detectable signal that relates to the amount of bound and/or unbound label, i.e., the amount of label bound or unbound to the GP73 antigen. The label is a molecule that produces or which may be induced to produce a signal. Examples of labels include fluorescers, enzymes, chemiluminescers, photosensitizers or suspendable particles. The signal is detected and may be measured by detecting enzyme activity, luminescence or light absorbance. Radiolabels may also be used and levels of radioactivity detected and measured using a scintillation counter.

Examples of enzymes which may be used to label the anti-human immunoglobulin include β-D-galactosidase, horseradish peroxidase, alkaline phosphatase, and glucose- 6-phosphate dehydrogenase ("G6PDH"). Examples of fluorescers which may be used to label the anti-human immunoglobulin include fluorescein, isothiocyanate, rhodamines, phycoerythrin, phycocyanin, allophycocyanin, o-phthaldehyde, fluorescamine, and Alexa Fluor® dyes (that is, sulfonated courmarin, rhodamine, xanthene, and cyanine dyes). Chemiluminescers include e.g., isoluminol. For example, the anti-human immunoglobulin may be enzyme labeled with either horseradish peroxidase or alkaline phosphatase.

Enzymes may be covalently linked to GP73 antigen reactive antibodies for use in the methods of the present invention using well known methods. There are many well known conjugation methods. For example, alkaline phosphatase and horseradish peroxidase may be conjugated to antibodies using glutaraldehyde. Horseradish peroxidase may also be conjugated using the periodate method. Commercial kits for enzyme conjugating antibodies are widely available. Enzyme conjugated anti-human and anti-mouse immunoglobulin specific antibodies are available from multiple commercial sources.

Biotin labeled antibodies may be used as an alternative to enzyme linked antibodies. In such cases, bound antibody would be detected using commercially available streptavidin-horseradish peroxidase detection systems.

Enzyme labeled antibodies produce different signal sources, depending on the substrate. Signal generation involves the addition of substrate to the reaction mixture. Common peroxidase substrates include ABTS (2,2'-azinobis (ethylbenzothiazoline-6-sulfonate)), OPD (O-phenylenediamine) and TMB (3,3', 5,5'-tetramethylbenzidine). These substrates require the presence of hydrogen peroxide. p-Nitrophenyl phospate is a commonly used alkaline phosphatase substrate. During an incubation period, the enzyme gradually converts a proportion of the substrate to its end product. At the end of the incubation period, a stopping reagent is added which stops enzyme activity. Signal strength is determined by measuring optical density, usually via spectrophotometer.

Alkaline phosphatase labeled antibodies may also be measured by fluorometry. Thus in the immunoassays of the present invention, the substrate 4-methylumbelliferyl phosphate (4-UMP) may be used. Alkaline phosphatase dephosphorylated 4-UMP to form 4-methylumbelliferone (4-MU), the fluorophore. Incident light is at 365 nm and emitted light is at 448 nm.

The amount of color, fluorescence, luminescence, or radioactivity present in the reaction (depending on the signal producing system used) is proportionate to the amount of autoantibodies in a sample which react with the GP73 antigen. Quantification of optical density may be performed using spectrophotometric or fluorometric methods, including flow cytometers. Quantification of radiolabel signal may be performed using scintillation counting.

In another exemplary embodiment, the assay is a competitive immunoassay, which employs one or more GP73-specific antibodies that binds to the same epitopes as the GP73-specific autoantibodies. In the assay, the GP73-specific antibodies and the GP73-specific autoantibodies in a sample compete for binding to the GP73 antigen. Typically, a constant amount of a labeled antibody which is known to bind to GP73 antigen is incubated with different concentrations of a sample from a subject. The GP73-specifc antibodies may be monoclonal or polyclonal.

As described herein above, the GP73-specific antibody may be labeled with a fluorescer, enzyme, chemiluminescer, photosensitizer, suspendable particles, or radioisotope. After incubation, bound labeled antibodies are separated from free antibodies. Depending on the signal producing system used and if necessary, an appropriate substrate with which the labeled antibody reacts is added and allowed to incubate. The signal generated by the sample is then measured. A decrease in optical density or radioactivity from before and after addition of the serum sample or between experimental and control samples, is indicative that autoantibodies in the sample have bound to the GP73 antigen. Decreased optical density or radiolabeled signal when compared to control samples from normal subjects correlates with a diagnosis of HCC in a subject.

In an alternative exemplary embodiment of the competitive immunoassay, an indirect method using two antibodies is provided. The first antibody is a GP73 antigen specific antibody as described in the preceding paragraph with the exception that it is not labeled. The first antibody is incubated with different concentrations of a sample from a subject. A constant amount of a second antibody is then added to the mixture of the sample and the first antibody. The second antibody recognizes constant regions of the heavy chains of the first antibody. For example, the second antibody may be an antibody which recognizes constant regions of the heavy chains of mouse immunoglobulin which has reacted with the GP73 antigen (anti-mouse immunoglobulin). The second antibody may be labeled with a fluorophore, chemilophore or radioisotope, as described above. Free labeled second antibody is separated from bound antibody. If an enzyme-labeled antibody is used, an appropriate substrate with which the enzyme label reacts is added and allowed to incubate. A decrease in optical density or radioactivity from before and after addition of the serum sample in comparison with control samples is indicative that autoantibodies in the serum sample have bound to the GP73 antigen. Decreased optical density or radioactivity when compared to control samples from normal subject correlates with a diagnosis of HCC in a subject.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to autoimmune or chronic inflammatory disease markers is utilized.

In some embodiments, the GP73-specific autoantibody level may be used together with other biological markers as a panel for HCC diagnosis. The panel allows for the simultaneous analysis of multiple markers correlating with liver disease, including HCC. For example, a panel may include markers identified as correlating with HBV, HCV or cirrhosis in a subject that is/are likely or not likely to respond to a given treatment. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

Since the diagnostic assay of the present invention is used for autoantibody detections, it should be understood that the antibodies can be directed to any GP73 epitope(s). Accordingly, there are no need to characterize any specific GP73 epitope to practice the present invention. Likewise, the autoantibodies may be of any variety as described elsewhere herein.

Data Analysis

In the present invention, a computer-based analysis program may also be used to translate the raw data generated by the detection assay into data of predictive value for a clinician. The clinician can readily access the predictive data using any suitable means. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication system). Once received by the profiling service, the sample is processed and a profile is produced, specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of a liver disease such as HCC to respond to a specific therapy) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or severity of disease.

Panel Assays

In addition to measuring the presence of GP73-specific autoantibodies alone, the present invention also contemplates "panel assays" measuring GP73 autoantibodies along with one or more other analytes, such as GP73 antigen, and/or COMP. Such panel assays may be provided as a kit containing two or more separate assay platforms or they may be combined on a single platform such as an immunoassay strip or ELISA plate.

EXAMPLES

Material and Methods

GP73 Protein

An inducible GP73-expressing plasmid (BACG81 obtained from St. Louis University, St. Louis, Mo.) was grown by standard methods. Briefly, glycerol stock was streaked on LB/amp (Luria-Bertani broth/Amplicillin) agar plates. A single colony was selected and inoculated in LB broth. Cells were grown and expanded until desired cell density was obtained. IPTG (isopropyl-1-thio-$\beta$-D-galactopyranoside) was added and cells were incubated for approx 4 hours. The cells were then harvested by centrifugation. The presence of GP73 in the harvested cell pellet was confirmed by SDS PAGE analysis. Recombinant His-tagged GP73 was isolated using standard techniques. Basically, the GP73 was extracted by the pellet under denaturing conditions and the GP73 protein purified from the lysate by passage over a nickel column. The protein was eluted from the column using an imidazole buffer solution. The purified recombinant GP73 protein was freed of imidazole by extensive dialysis.

Specimens

Sera from individuals with a variety of clinically documented liver disease, including viral and non-viral hepatitis, were tested for the presence of GP73-specific autoantibodies as well as a GP73 antigen, cartilage oligomeric protein (COMP), and other markers of liver disease.

Assays

COMP was assayed using a commercially available kit distributed by INOVA Diagnostics, Inc. GP73 antigen was detected in a capture ELISA assay format. GP73-specific autoantibody was measured using GP73 autoantibody ELISA.

For GP73 antigen determination, a rabbit anti-GP73 antibody was coated on to the wells of a polystyrene microtiter plate in carbonate buffer. Patient sera were diluted 1:101 in a dilution buffer and incubated for 1 hr at room temperature. Following the incubation, the plate was washed with an ELISA wash buffer. Mouse anti-GP73 monoclonal antibody was then added and then incubated for 30 minutes at room temperature. At the completion of incubation, the plate was washed with a wash buffer and goat anti-mouse-horseradish peroxidase was added. Following a 30 incubation, TMB substrate was added and incubated for 30 minutes, the reaction stopped with an ELISA stop buffer, and the O.D. was read at 495 nm in a spectrophotomer.

For GP73-specific autoantibody determination, polystyrene microtiter plates were coated with GP73 antigen overnight at 5° C. Plates were washed with an ELISA wash buffer and 100 µL of an ELISA blocking buffer was then added. Plates were blocked for 1 hour and then washed with an ELISA wash buffer. Plates were dried overnight. Autoantibody was detected by adding sera diluted 1:101 in a dilution buffer. Following a 30-minute incubation, the plates were washed, and goat anti-human IgG-horseradish peroxidase conjugate was added. Following 30 minute incubation, the plates were washed, and TMB substrate added for 30 minutes. The reaction was stopped by added an ELISA stop buffer and the resulting color was read on a spectrophotometer at 495 nm.

Results

Figure 1:
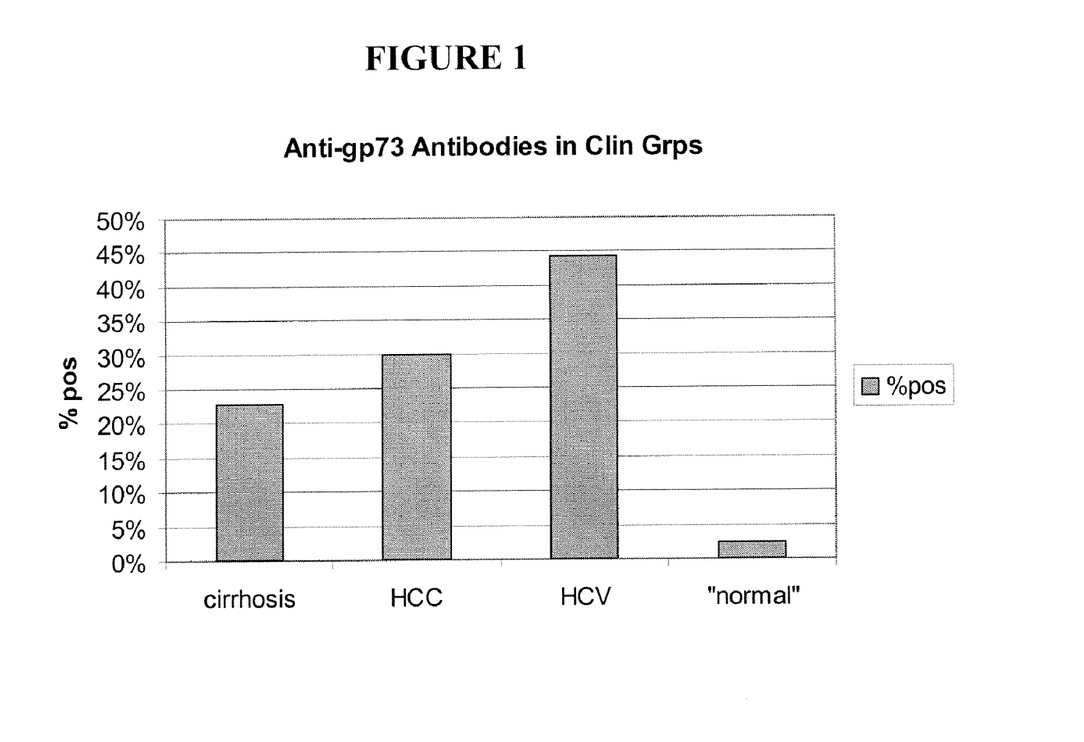
FIG. 1 shows the percentages of positives identified based upon the level of GP73-specific autoantibodies in three liver diseases (cirrhosis, HCC, and HCV) in comparison with normal subjects.
Figure 2:
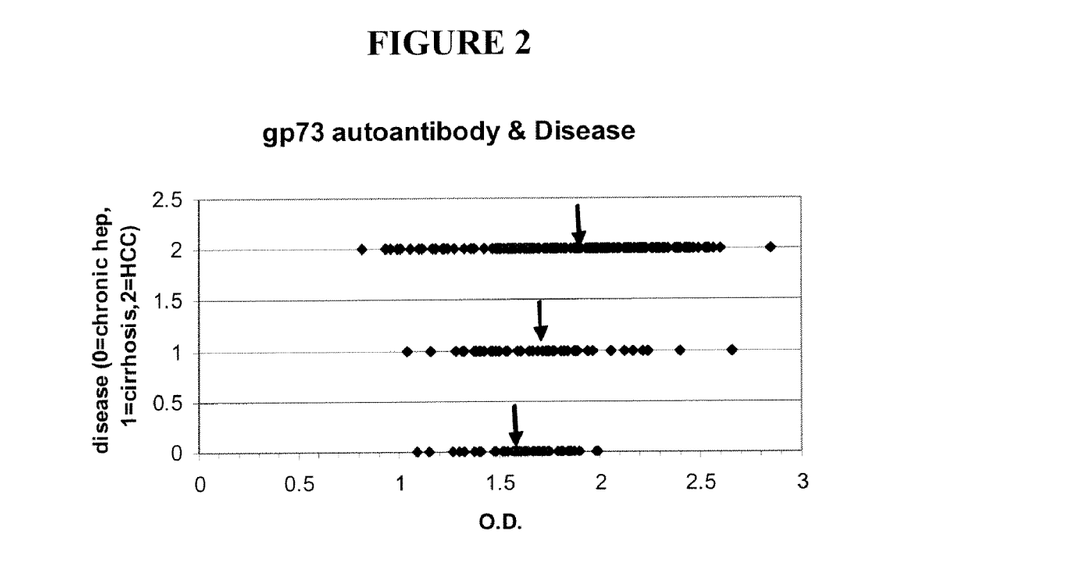
FIG. 2 shows the distribution of the levels of GP73-specific autoantibodies in three liver diseases-cirrhosis, HCC, and HCV.

The utility of detection of GP73 autoantibody (anti-GP73) was assessed on sera from 3 clinical centers, which were obtained from St. Louis University, St. Louis, Mo. The first clinical group consisted of 22 patients with cirrhosis, 10 patients with HCC, and 9 patients with HCV. Thirty-nine healthy controls were also evaluated. As shown in FIG. 1 and Table 1, although anti-GP73 antibodies could be detected in each of the groups, the frequency of values greater than 0.5 O.D. ranged from 23 to 44% in the liver disease sera compared to a frequency of only 3% in the healthy control group.

TABLE 1

Frequency of anti-GP73 autoantibody In Liver Disease and Healthy Control Sera

| Disease | Total | Num. Positives | % Positives (c/o = 0.5) |
| --- | --- | --- | --- |
| Cirrhosis | 22 | 5 | 23% |
| HCC | 10 | 3 | 30% |
| HCV | 9 | 4 | 44% |
| Control | 39 | 1 | 3% |

The second clinical group is a well-characterized cohort of approximately 270 sera from patients with chronic hepatitis, cirrhosis, or HCC, which was obtained from Ospedale Margiagall, Milan, Italy. This group was tested for GP73 autoantibodies. The results showed the median O.D. for GP73 antibodies was clearly higher than that in patients with cirrhosis or chronic hepatitis.

TABLE 2

Mean and Median Optical Density (O.D.) of Anti-GP73 Autoantibody Detected in Liver Disease and Healthy Control Sera

| Diseases | GP73 mean OD | GP73 median OD |
| --- | --- | --- |
| Chron. Hepatitis | 1.61 | 1.62 |
| Cirrhosis | 1.70 | 1.70 |
| HCC | 1.90 | 1.96 |

Figure 3:
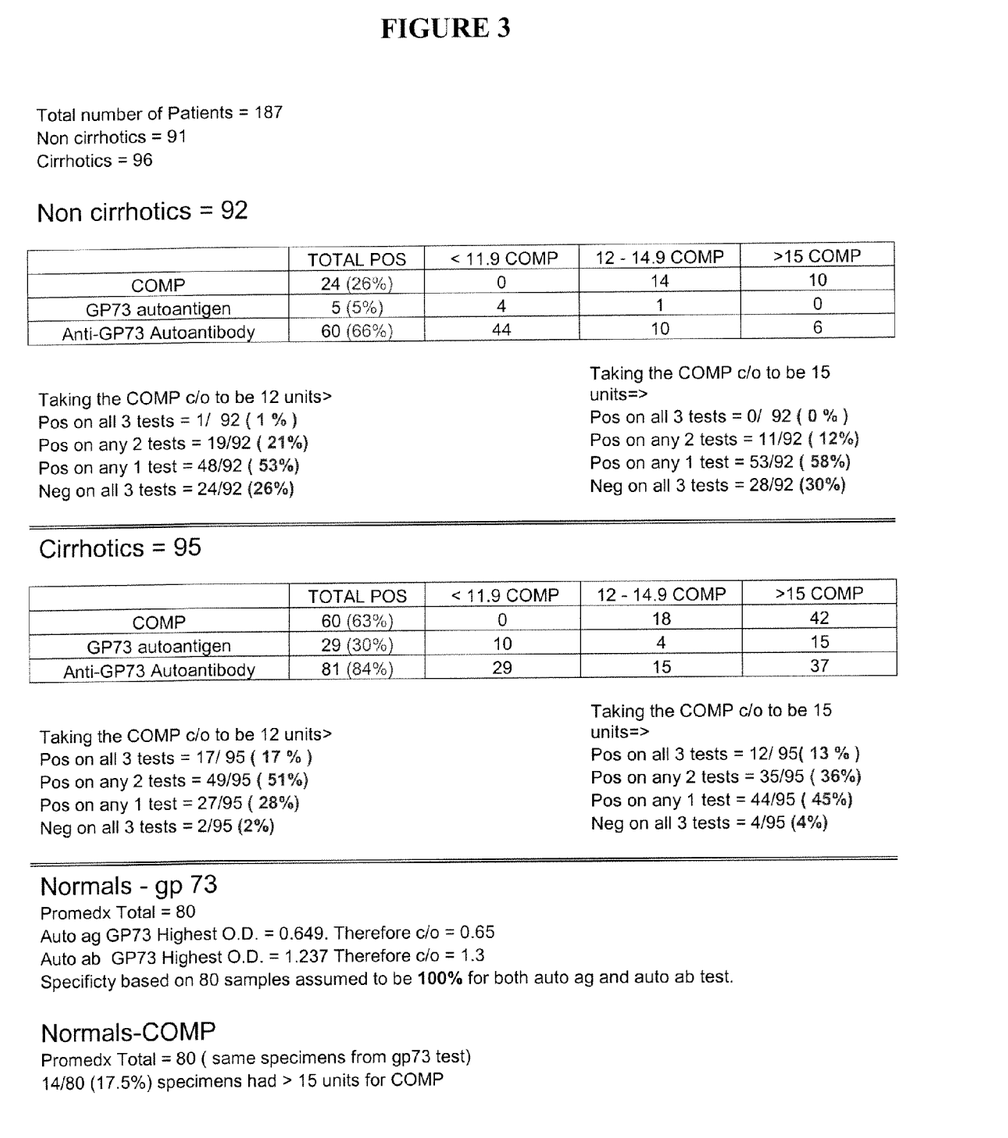
FIG. 3 shows the comparison of three methods (cartilage oligomeric protein (COMP), GP73 antigen detection, and GP73 antibody detection) in the analysis of 187 patients consisting of 91 patients without cirrhosis and 96 patients with cirrhosis.
Figure 4A:
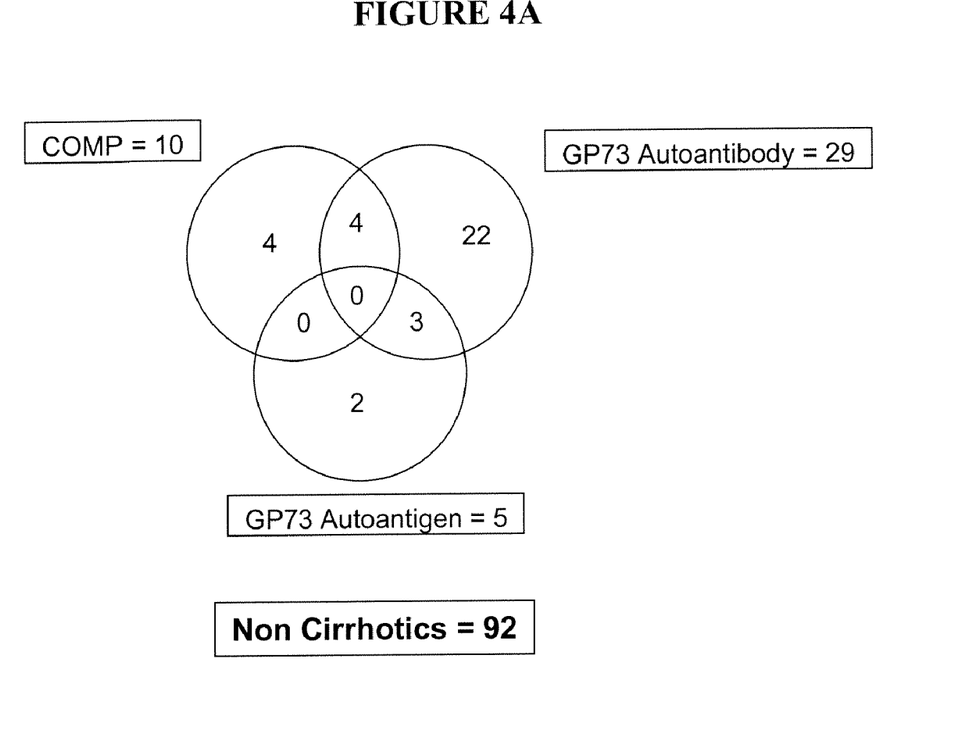
Figure 4B:
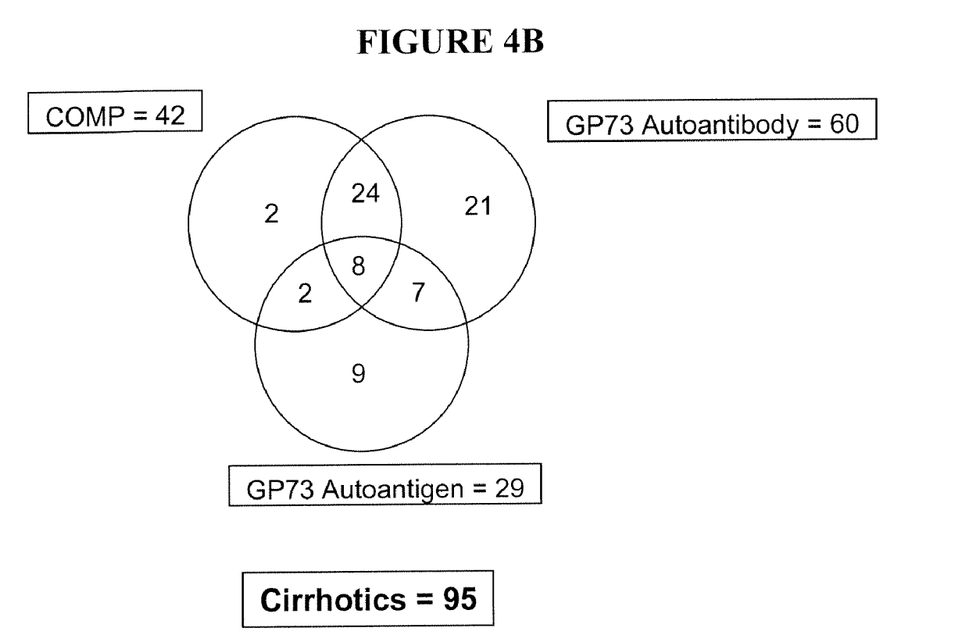
Figure 5:
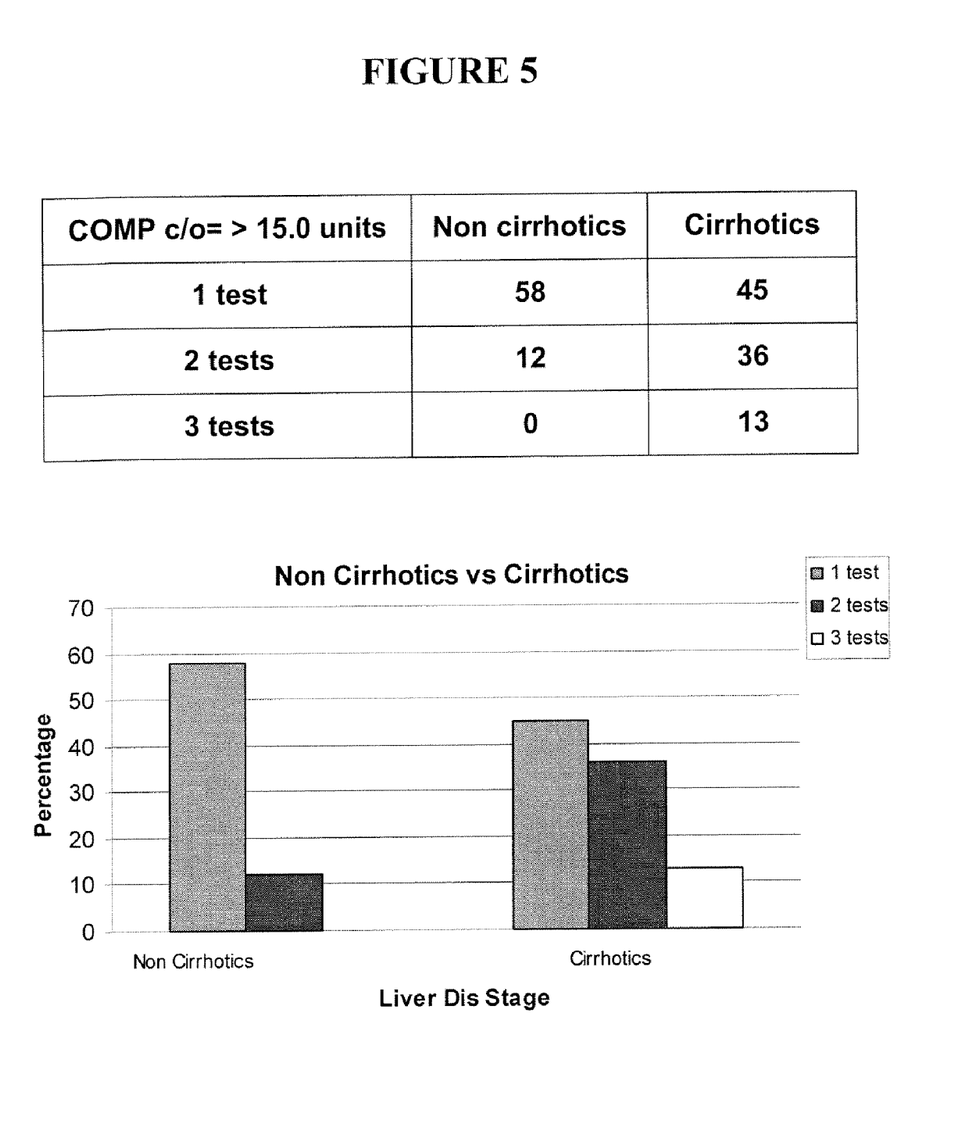
FIG. 5 shows the distributions of patients according to the number of positive responses to the three diagnostic tests for each patient.

The third group was a cohort of 187 patients consisting of 91 patients without cirrhosis and 96 patients with cirrhosis, which was obtained from Kings College, London, England (FIG. 3). This group was tested for the presence or anti-GP73 antibodies. In addition, specimens from those patients were also tested for serum GP73 antigen and COMP. The results showed that GP73 autoantibodies were more frequent (84%) in cirrhotic than in non-cirrhotic patients (66%) (FIG. 4 and FIG. 5).

The value of testing several parameters and using the combined results to assess the patients was also examined. It was found that while 14% of the cirrhotic patients were positive for GP73 autoantibody, GP73 antigen, and COMP, none of the non-cirrhotic patients were positive for all 3 assays. Conversely, it was found that while only 4% of the cirrhotic patients were negative for all three assays, 30% of the non-cirrhotic patients were negative for all 3 assays. In addition, 39 healthy controls were negative by both the GP73 autoantibody and GP73 antigen assays.

The examples set forth above are provided to give those of ordinary skill in the art with a complete disclosure and description of how to make and use the preferred embodiments of the present invention, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

REFERENCES

1. Kladney, R. D., et al., "GP73, a novel Golgi-localized protein upregulated by viral infection" Gene 249, 53-65 (2000)
2. Iftikhar, R., et al., "Disease- and cell-specific expression of GP73 in human liver disease" Am. J. Gastroenterol. 99, 1087-95 (2004)
3. Kladney, R. D., et al., "Expression of GP73, a resident Golgi membrane protein, in viral and nonviral liver disease" Hepatology 35, 1431-40 (2002)
4. Block, T. M., et al., "Use of targeted glycoproteomics to identify serum glycoproteins that correlate with liver cancer in woodchucks and humans" Proc. Natl. Acad. Sci. U.S.A. 102, 779-84 (2005)
5. Kladney, R. D., et al., "Upregulation of the Golgi protein GP73 by adenovirus infection requires the E1A CtBP interaction domain" Virology 301, 236-46 (2002)
6. Marrero, J. A., et al., "GP73, a resident Golgi glycoprotein, is a novel serum marker for hepatocellular carcinoma" J. Hepatol. 43, 1007-12 (2005)

What is claimed is:
1. A method for detecting Golgi membrane protein 73 (GP73) autoantibodies in a subject comprising the steps of:
   a. preparing a GP73 protein;
   b. reacting the GP73 protein with a serum or plasma sample from the subject; and
   c. detecting the GP73 autoantibodies in the sample.

* * * * *